United States Patent [19]
Sutter

[11] Patent Number: 5,122,139
[45] Date of Patent: Jun. 16, 1992

[54] MEDICAL COAGULATION INSTRUMENT

[75] Inventor: Hermann Sutter, Gundelfingen, Fed. Rep. of Germany

[73] Assignee: Select-Medizintechnik Hermann Sutter GmbH, Freiburg, Fed. Rep. of Germany

[21] Appl. No.: 613,317

[22] Filed: Nov. 8, 1990

[30] Foreign Application Priority Data

Nov. 13, 1989 [DE] Fed. Rep. of Germany ....... 3937700

[51] Int. Cl.$^5$ .............................................. A61B 17/50
[52] U.S. Cl. ......................................... 606/51; 606/52
[58] Field of Search ................ 606/32, 34, 37, 39–42, 606/49–52

[56] References Cited

U.S. PATENT DOCUMENTS

| | | | |
|---|---|---|---|
| 3,100,489 | 8/1963 | Bagley | 606/52 |
| 4,461,297 | 7/1984 | Sutter | 128/321 |
| 4,732,149 | 3/1988 | Sutter | 128/303 |

FOREIGN PATENT DOCUMENTS 2019891 11/1971 Fed. Rep. of Germany .
2627679 1/1977 Fed. Rep. of Germany .
3640471 6/1988 Fed. Rep. of Germany .

*Primary Examiner*—Stephen C. Pellegrino
*Assistant Examiner*—Steven J. Shumaker
*Attorney, Agent, or Firm*—Peter K. Kontler

[57] ABSTRACT

A bipolar coagulation forceps wherein the switch at the inner side of one of its legs can be closed by an actuator at the inner side of the other leg. The switch and the actuator have cooperating centering and guide elements which engage one another to prevent any shifting of the jaws at the working ends of the legs during that stage of pivoting of the legs when the jaws already engage each other but the pivoting of the legs relative to each other must continue in order to close the switch. The latter is connected with a terminal at the rear ends of the legs by a conductor which is confined in a tube at the inner side of the leg carrying the switch. The outer side of the leg which carries the actuator has a finger-receiving flute which enhances the flexibility of the respective leg and renders it possible to pivot the legs relative to each other subsequent to engagement of the jaws with one another.

16 Claims, 1 Drawing Sheet

Fig. 1
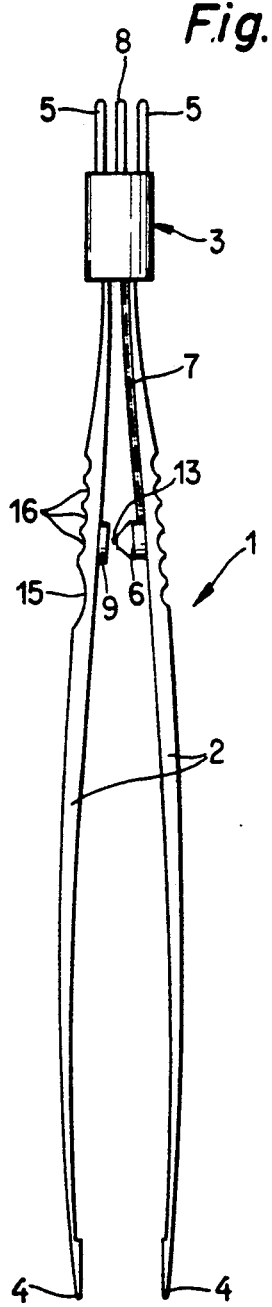
Fig. 4
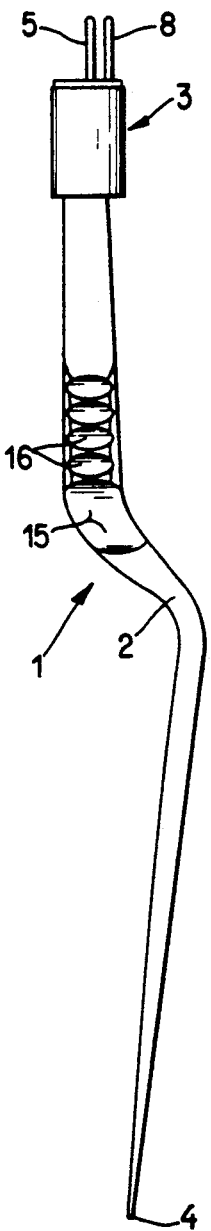
Fig. 2
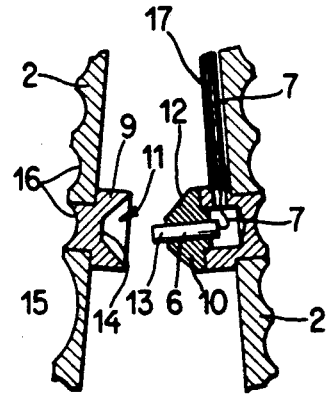
Fig. 3
Fig. 5
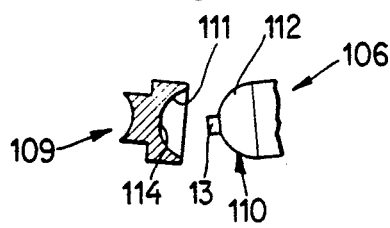
Fig. 6
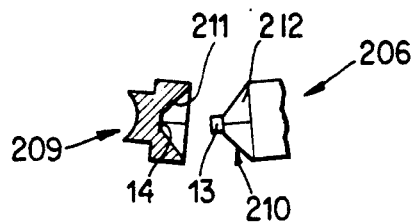

MEDICAL COAGULATION INSTRUMENT

BACKGROUND OF THE INVENTION

The invention relates to improvements in bipolar medical coagulation instruments of the type disclosed, for example, in U.S. Pat. No. 4,732,149 granted Mar. 22, 1988 to Sutter for "Bipolar Medical Coagulation Instrument". The disclosure of this patent is incorporated herein by reference.

A bipolar medical coagulation instrument normally comprises a forceps with two elongated legs each having a jaw at one end and an electric terminal at the other end. The legs are electrically insulated from each other. A switch which is carried by one of the legs is closed in response to pivoting of the legs in directions to engage the two jaws with one another and additional pivoting while the jaws continue to engage each other. The switch is provided at the inner side of the one leg and is connected with a third terminal by a conductor which ensures that the forceps receives high-frequency electrical energy in response to actual closing of the switch. As a rule, the switch comprises one or more projections which can be caused to engage blank surfaces when the switch is closed to thus establish an electrical connection with the high-frequency generator. The conductor which connects the switch with the third terminal is glued to the respective leg of the forceps or is loosely inserted into a shrinkable hose which surrounds the one leg. The hose is desirable and advantageous because it ensures reliable insulation of the forceps. However, if the shrinking of the hose does not result in the making of an envelope3 which closely follows the outline of the one leg in the region of the switch, foreign matter (such as a cleaning fluid) is likely to penetrate into the improperly shrunk hose. The cleaning fluid can cause additional stretching of and actual damage to the hose.

Bonding of the conductor to the one leg of the forceps is not always satisfactory because the adhesive which is used to bond the conductor to the forceps cannot stand those temperatures which are necessary during shrinking of insulating hoses onto the legs of the forceps.

Another drawback of heretofore known bipolar medical coagulation instruments is that their jaws are likely to assume improper positions (e.g., by overlapping or crossing each other) as a result of that additional pivoting of the legs which is needed to close the switch subsequent to movement of the jaws into engagement with one another. Misalignment of jaws is likely to take place if the jaws are pointed and very narrow, a configuration which is often necessary in order to carry out a particular coagulating operation. Even minor shifting of the jaws from their optimum positions relative to each other can effect the coagulating operation.

OBJECTS OF THE INVENTION

An object of the invention is to provide a novel and improved bipolar medical coagulation instrument wherein the likelihood of misalignment of jaws during any stage of pivoting of the legs of the forceps is reduced or eliminated in a simple but reliable manner.

Another object of the invention is to provide a novel and improved forceps wherein the positions of the jaws relative to each other remain unchanged during the last stage of pivoting of the legs relative to one another in order to close the switch which controls the supply of high-frequency energy to the legs.

A further object of the invention is to provide a novel and improved switch for use in the above outlined instrument.

An additional object of the invention is to provide novel and improved legs which form part of the above outlined medical instrument.

Still another object of the invention is to provide novel and improved means for shielding the conductor which connects the switch with the corresponding terminal of the above outlined medical instrument.

An additional object of the invention is to provide the instrument with a switch and with a switch actuator which can perform additional important and desirable functions.

Another object of the invention is to provide a novel and improved method of guiding the legs of a forceps during pivoting in directions to move their jaws into engagement with one another.

SUMMARY OF THE INVENTION

The invention is embodied in a bipolar medical instrument which comprises a forceps having first and second elongated legs. Each leg constitutes a coagulation electrode and has a jaw at one of its ends and an electric terminal at the other end. The legs are pivotable relative to each other at their other ends in order to move the jaws into and from engagement with each other. The instrument further comprises an electrical insulator between the other ends of the legs, a third terminal at the other ends of the legs, a normally open electric switch member which is provided on the first leg between its ends, conductor means connecting the switch member with the third terminal, and an actuator member provided on the second leg opposite the switch member and having means for closing the switch member in response to pivoting of the legs relative to each other and subsequent to engagement of the jaws with one another. In other words, at least some additional pivoting—after the two jaws jaws already engage each other—is needed in order to actually close the switch member and to thus connect the electrodes with a source of high-frequency energy when the forceps is to be used as a coagulation instrument.

In accordance with a desirable and advantageous feature of the invention, at least one of the two (switch and actuator) members includes means for centering and guiding the members relative to each other, at least during engagement of the jaws with one another and during further pivoting of the legs in order to close the switch member. The centering means can comprise a male centering element on one of the members and a complementary female centering element on the other member. For example, the female centering element can include a socket in the actuator member, and the male centering element can include a projection on the switch member. The male centering element can be provided with a convex surface or includes a conical or pyramidal projection, and the female centering element is then provided with a complementary concave surface or a complementary conical or pyramidal socket for the respective male centering element.

The switch member can include a housing which is at least partially confined in the actuator member when the jaws engage each other.

The outer side of at least one of the legs (namely that side which faces away from the other leg) can be provided with a finger-receiving flute which is adjacent the respective (switch or actuator) member. The flute can be provided at the outer side of the second leg adjacent the actuator member, preferably between the actuator member and the jaw of the second leg. At least the one (fluted) leg of the instrument is preferably resilient and flexible and its flexibility is enhanced by the provision of a flute in its outer side. This renders it possible to pivot the legs relative to each other subsequent to engagement of the two jaws with one another, i.e., the resilient leg or legs can undergo temporary deformation in the regions between their terminals and their jaws to thus enable the closing means of the actuator member to close the switch member while the positions of the (engaged) jaws remain unchanged.

The outer side of at least one of the legs can be provided with additional flutes or other unevennesses (e.g., in the form of ribs and grooves, serrations or the like) to ensure that the legs can be properly grasped by the hand of the person using the forceps. The additional flutes are adjacent the respective (switch or actuator) member.

The aforementioned conductor means is preferably provided at the inner side of the first leg, i.e., at that side which confronts the second leg. The instrument preferably further comprises an enclosure for the conductor means; such enclosure can include a tube, particularly a metallic tube.

The novel features which are considered as characteristic of the invention are set forth in particular in the appended claims. The improved medical instrument itself, however, both as to its construction and the mode of using the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a side elevational view of a medical instrument which constitutes a forceps and embodies one form of the present invention;

FIG. 2 is an enlarged fragmentary central longitudinal sectional view of the switch member, of the actuator member and of the adjacent portions of the legs, the switch member being shown in open position;

FIG. 3 illustrates the structure of FIG. 2 but with the switch member in closed position;

FIG. 4 is an end elevational view of the medical instrument;

FIG. 5 is an elevational view of a modified switch member an a sectional view of the associated actuator member; and FIG. 6 is an elevational view of a third switch member and a sectional view of the associated actuator member.

DESCRIPTION OF PREFERRED EMBODIMENTS

The medical instrument 1 which is shown in FIGS. 1 to 4 is a bipolar forceps with two elongated legs 2 each having a jaw 4 at its working or front end and an electric terminal 5 at the other or rear end. The legs 2 are electrically separated from each other by an insulator 3 which is adjacent the terminals 5 and carries a third terminal 8. The insulator 3 constitutes a fulcrum for the legs 2 which are pivotable relative to each other in order to engage the two jaws 4. In addition, the major portions of the legs 2 are pivotable relative to each other after the two jaws 4 are already in engagement with one another, and such pivoting of the legs 2 is necessary in order to close an electric switch 6 which is provided at the inner side of the right-hand leg 2 of FIGS. 1 to 3 opposite an actuator 9 at the inner side of the left-hand leg. An electrical conductor 7 serves to connect the switch 6 with the third terminal 8 on the insulator 3. As can be seen in FIGS. 1 and 4, the third terminal 8 is located between but is not in line with the terminals 5.

The jaws 4 serve to engage a piece of tissue, a vessel or another structure prior to connection of the forceps 1 with a high-frequency generator, i.e., prior to closing of the switch 6 by the actuator 9. The coagulating operation begins while the engaged tissue, vessel or another part is held by the jaws 4 and the mobile portion 13 in the housing 10 of the switch 6 is depressed by a switch closing surface 14 of the actuator 9. The design of the forceps 1 is preferably such that the person in charge continues to apply pressure against the outer sides of median portions of the legs 2 and gradually increases such pressure following engagement of the jaws 4 until the surface 14 effects a certain depression of the movable switch portion 13 which is needed to actually close the switch 6.

The illustrated switch 6 is a separately produced component which is installed in the median portion of the respective leg 2 and confronts the actuator 9. The latter also constitutes a separately produced component which is installed in the median portion of the corresponding leg 2. However, it is equally within the purview of the invention to provide an actuator which is an integral part of the respective leg 2, e.g., if the legs are formed in a stamping, forging or like machine.

In accordance with a feature of the invention, the switch 6 is provided with a male centering element 12 which is an integral projection of the switch housing 10, and the actuator 9 is provided with a complementary female centering element in the form of a centrally located socket 11 facing the housing 10. The manner in which the male centering element 12 fills the socket 11 when the switch 6 is actually closed is shown in FIG. 3; at such time, the surface 14 maintains the movable switch portion 13 in an axial position in which the switch 6 is closed.

It will be seen that the actuator 9 confines a substantial portion of the switch housing 10 when the switch 6 is closed. This ensures that the two legs 2 of the forceps 1 are maintained in predetermined optimum positions relative to each other in the course of the coagulating step. The socket 11 of the actuator 9 is bounded by a conical surface which is complementary to the conical external surface of the male centering element 12.

FIG. 5 shows that the socket 111 of the actuator 109 can be bounded by a concave surface which is complementary to the convex external surface of the male centering element 112 on the housing 110 of the switch 106. Furthermore, and as shown in FIG. 6, it is possible to provide a switch 206 with a housing 210 including a male centering element 212 having a pyramidal external surface which is complementary to the pyramidal internal surface bounding the socket 211 of the actuator 209. The cone 12 of FIGS. 1-3 is a truncated cone, and the pyramid 212 of FIG. 6 is a truncated pyramid. The flat tops of these parts abut or are immediately adjacent the surface 14, 114 or 214 at the bottom of the respective socket 11, 111 or 211 when the switch 6, 106 or 206 is closed.

Since the fulcrum for the legs 2 of the forceps 1 is located at the insulator 3, the switch 6 and the actuator 9 move along arcuate paths when the operator applies pressure against the outer sides of the legs 2 in order to move the jaws 4 toward engagement with each other and to thereupon continue with pivoting of the legs in order to close the switch 6. Such movements of the actuator 9 and switch 6 along arcuate paths render it possible to engage the male centering element 12 with the female centering element including the socket 11 even before the switch 6 is actually closed, i.e., at least from the instant on when the jaws 4 have been moved into actual engagement with one another. This is desirable and advantageous because the male and female centering elements maintain the engaged jaws 4 in optimum positions relative to each other while the median portions of the legs 2 continue to pivot toward each other for the purpose of closing the switch 6. Thus, the jaws 4 are not likely to cross each other or to otherwise move relative to one another during the interval between their initial engagement and actual closing of the switch 6.

The outer side of the leg 2 which carries the actuator 9 is provided with a transversely extending finger-receiving recess or flute 15 which is closely adjacent the actuator and is located between the actuator and the respective jaw 4. Thus, the actuator 9 is disposed between the flute 15 and the insulator 3. The flute 15 not only permits reliable and optimum grasping of the respective portion of that leg 2 which carries the actuator 9 but also weakens or renders more flexible the corresponding median portion of the respective leg so that the latter can be more readily flexed subsequent to engagement of the jaws 4 and during movement of the actuator 9 and switch 6 toward each other for the purpose of filling the socket 11 by the male centering element 12 and of ultimately closing the switch. A similar flute can be provided at the outer side of the leg 2 which carries the switch 6 in lieu of the illustrated flute 15, or each of the two legs can be provided with a flute 15.

FIGS. 1 to 4 show that the outer sides of both legs 2 are provided with additional flutes 16 or analogous depressions which facilitate grasping of the corresponding portions of the legs in actual use of the forceps 1. The flutes 16 are shallower than the flute 15, and the flutes 16 at the outer side of the leg 2 which carries the actuator 9 are disposed between the flute 15 and the insulator 3. The flutes 16 can also serve to reduce the resistance of median portions of the legs 2 to flexing and thus enable the fingers which engage the outer sides of the two legs at or close to the actuator 9 and switch 6 to gradually pivot the legs subsequent to engagement of the jaws 4 with one another. The legs 2 are made of a resilient material.

The flute 15 in the leg 2 which carries the actuator 9 is nearer to the center of this leg than the actuator and the switch 6. However, the flute 15 is still nearer to the insulator 3 than to the jaws 4. The exact distance of the flute 15 from the insulator 3, jaws 4, actuator 9 and switch 6 depends on resiliency of the material of the legs 2 and is selected with a view to ensure the aforediscussed sequence of steps in response to the application of pressure against the surface bounding the flute 15 and against the external surface of the other leg 2 opposite the flute 15. Thus, the initial application of pressure entails a movement of the jaws 4 toward and against each other, and the next stage involves deformation of the legs 2 while the jaws 4 continue to contact each other. The centering means including the surface bounding the socket 11 in the actuator 9 and the projection 12 of the housing 10 of the switch 6 becomes effective not later than when the jaws 4 engage one another and remains effective while the legs 2 continue to pivot relative to each other for the purpose of closing the switch 6. The application of pressure against the surface bounding the flute 15 and against the aligned portion of external surface of the right-hand leg 2 of FIG. 1 is increased gradually subsequent to engagement of the jaws 4 with each other in order to cause the surface 14 to depress the movable portion 13 of the switch 6 to the position of FIG. 3 in which the switch is closed. It has been found that weakening of the left-hand leg 2 of FIG. 2 due to provision of the flute 15 enhances the softness or flexibility of this leg to a desired extent and permits closing of the switch 6 in response to gradual rise in the magnitude of the applied force. To summarize, the flute 15 brings about at least three important advantages. First, the operator knows where to apply finger pressure to the outer side of the leg 2 which carries the actuator 9. Secondly, the surface bounding the flute 15 reduces the likelihood of slippage of the finger along the outer side of the respective leg 2. Thirdly, the flexibility of the corresponding portion of the left-hand leg 2 of FIG. 1 is increased with the aforediscussed advantages concerning gradual rise of the pressure which must be applied in order to close the switch 6. Such gradual rise of pressure, combined with the action of the aforediscussed centering means, greatly reduces the likelihood of misalignment of the jaws 4 relative to each other during that stage of pivoting of the legs 2 which is required to close the switch 6.

The flute 15 constitutes the foremost and deepmost flute of a series of flutes which include the flute 15 and the set of adjacent flutes 16 in the outer side of the leg 2 which carries the actuator 9. The flutes 16 serve to provide room for insertion of one or more fingers while another finger extends into the flute 15. All this further reduces the likelihood of slippage of the fingers relative to the legs 2 when the improved forceps 1 is in actual use. The flute 15 can receive a portion of an index finger, and an adjacent flute 16 can receive a portion of another finger adjacent the index finger.

FIGS. 1 to 3 show that the conductor 7 between the housing 10 of the switch 6 and the corresponding terminal 8 is surrounded by an elongated enclosure 17 which preferably constitutes a metallic tube. This tube is adjacent the inner side of the leg 2 which carries the switch 6. The legs 2 are surrounded by hoses of insulating material which are shrunk in a manner known from the art of making forcepses, and the hose which surrounds the right-hand leg of FIG. 1 closely follows the outline of the tube 17. The latter shields the conductor 7 all the way between the switch housing 10 and the terminal 8. An advantage of the metallic tube 17 is that it can readily stand the temperatures which are necessary to ensure satisfactory shrinkage of insulating material onto the legs 2 of the improved forceps 1. The tube 17 is confined in the insulating jacket for the respective leg 2 so that it does not interfere with cleaning of the forceps and/or with other manipulations.

U.S. Pat. No. 4,461,297 granted Jul. 24, 1984 to Sutter for "Forceps" discloses guide means extending from the inner sides of the legs and being telescoped into each other to ensure predictable movements of the respective portions of the legs during pivoting in directions to move the jaws toward or away from each other. However, the guide means in the patented forceps are not provided on a switch and/or on an actuator for a switch. The switch 6 and the applicator 9 in the forceps 1 of the present invention perform their normal functions and, in addition, carry or embody complementary male and female centering elements to ensure proper guidance of the legs 2 during pivoting in a direction to first move the jaws 4 into engagement with each other and to thereupon maintain the jaws in optimum positions relative to each other during the last stage of pivoting toward positions in which the switch 6 is closed.

An important advantage of the improved forceps is that it is not necessary to machine and affix discrete centering elements. Thus, all that is necessary is to configurate the switch 6 and the actuator 9 in such a way that one of these members carries a female centering element and the other of these members carries a complementary male centering element. This contributes to simplicity and lower cost of the improved forceps. Moreover, it is possible to provide relatively large male and female centering elements to thus further enhance the ability of such centering elements to adequately guide the legs 2 during pivoting toward the positions which are shown in FIG. 3, namely toward the positions in which the jaws 4 engage each other and the switch 6 is closed subsequent to movement of the jaws into engagement with one another. Adequate male and female centering elements can be provided regardless of whether the switch 6 and the actuator 9 are integral (e.g., stamped) parts of the respective legs 2 or are separately produced parts which are affixed to the respective legs in a separate step.

The configurations of the male and female centering elements (portions 12, 112, 212 of the respective housings 10, 110, 210 and the corresponding sockets 11, 111, 211) exhibit the advantage that the centering elements do not interfere with movements of the corresponding portions of the legs 2 along arcuate paths. Thus, the conical projection 12 can begin to enter the aligned socket 11 not later than when the jaws 4 come into actual engagement with each other and during subsequent pivoting of the legs 2 for the purpose of closing the switch 6. As mentioned above, the surface bounding the socket 11 can be contacted by the exposed surface of the male centering element (projection 12) while the legs 2 continue to pivot relative to each other subsequent to engagement of the jaws 4 and preparatory to closing of the switch 6.

The leg 2 which carries the actuator 9 and/or the other leg 2 can be weakened in a number of ways, i.e., not necessarily by the flute or flutes 15. However, weakening of at least one of the legs 2 as a result of the provision of a flute 15 therein is preferred at this time because the flute 15 can perform several additional desirable and advantageous functions, such as guiding the finger which applies pressure in the region of the actuator 9 and pinpointing the locus of application of finger pressure. The flute 15 ensures that a relatively small force suffices to flex the respective leg 2 in the region of the actuator 9 when the jaws 4 already engage each other but the median portions of the legs 2 must be pivoted toward each other in order to close the switch 6.

As a rule, the switch 6 is placed rather close to the terminals 5 and 8. Therefore, it is presently preferred to place the flute or flutes 15 between the switch 6 and the actuator 9 on the one hand and the jaws 4 on the other hand. This renders it possible to flex the legs 2 in response to the exertion of a relatively small force. Such force is necessary to move the median portions of the legs 2 relative to each other while the distance between the front ends of the legs remains unchanged because the jaws 4 already abut each other. Gradual rise of force which flexes the median portion of the legs 2 subsequent to engagement of the jaws 4 with each other is desirable on several grounds. Thus, the jaws 4 are less likely to shift positions relative to each other and the coagulating step is simplified.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A bipolar medical instrument, comprising a forceps having first and second elongated legs each of which constitutes a coagulation electrode having a jaw at one end and a terminal at the other end, said legs being pivotable relative to each other at said other ends to move said jaws into and from engagement with each other; an electrical insulator between the other ends of said legs; a third terminal at said other ends; a normally open electric switch member provided on said first leg between the ends thereof; conductor means connecting said switch member to said third terminal; and an actuator member provided on said second leg opposite said switch member and having means for closing said switch member in response to pivoting of said legs relative to each other and subsequent to engagement of said jaws with one another, said members including means for centering said members, said centering means of said members cooperating to center said members relative to each other at least during engagement of said jaws with one another.

2. The medical instrument of claim 1, wherein said centering means comprise a male centering element on one of said members and a complementary female centering element on the other of said members.

3. The medical instrument of claim 2, wherein said female centering element includes a socket in said actuator member and said male centering element comprises a projection on said switch member.

4. The medical instrument of claim 2, wherein said male centering element has a convex surface and said female centering element has a complementary concave surface.

5. The medical instrument of claim 2, wherein said male centering element includes a conical projection and said female centering element has a complementary socket for said conical projection.

6. The medical instrument of claim 2, wherein said male centering element includes a pyramidal projection and said female centering element has a complementary socket for said pyramidal projection.

7. The medical instrument of claim 1, wherein said switch member includes a housing which is at least partially confined in said actuator member when said jaws engage each other.

8. The medical instrument of claim 1, wherein said closing means is positioned to engage and close said switch member subsequent to engagement of said jaws with one another and in response to further pivoting of said legs relative to each other.

9. The medical instrument of claim 1, wherein at least one of said legs has an outer side facing away from the other of said legs and provided with a finger-locating flute adjacent the respective member.

10. The medical instrument of claim 9, wherein said flute is provided in the outer side of said second leg adjacent said actuator member intermediate said actuator member and the jaw of said second leg.

11. The medical instrument of claim 9, wherein at least said at least one leg is resilient and flexible and its flexibility is enhanced by said flute, said jaws engaging one another in response to pivoting of said legs relative to one another in a direction to move said members toward each other and said closing means being operative to close said switch member in response to resilient deformation of said resilient leg following engagement of said jaws with each other.

12. The medical instrument of claim 9, wherein said outer side is further provided with additional flutes adjacent the respective member.

13. The medical instrument of claim 9, wherein each of said legs has an outer side facing away from the other leg and each of said outer sides has a plurality of flutes adjacent the respective member.

14. The medical instrument of claim 1, wherein said first leg has an inner side confronting said second leg and said conductor means is adjacent said inner side, and further comprising an enclosure for said conductor means.

15. The medical instrument of claim 14, wherein said enclosure comprises a tube.

16. The medical instrument of claim 14, wherein said enclosure includes a metallic tube.

* * * * *